United States Patent [19]
Witt

[11] Patent Number: 4,785,170
[45] Date of Patent: Nov. 15, 1988

[54] METHOD AND APPARATUS FOR THE ON-LINE MEASUREMENT OF TRANSMISSION OR REFLECTION ON MOVING OBJECTS IN THE RANGE OF DETECTABLE ELECTROMAGNETIC RADIATION

[75] Inventor: Wolfgang F. Witt, Clausthal-Zellerfeld, Fed. Rep. of Germany

[73] Assignee: Pantuc Inc. -Büro Stephan Röthele, Clausthal-Zellerfeld, Fed. Rep. of Germany

[21] Appl. No.: 915,611

[22] Filed: Oct. 6, 1986

[30] Foreign Application Priority Data

Oct. 4, 1985 [DE] Fed. Rep. of Germany ....... 3535515

[51] Int. Cl.$^4$ .......................... G01J 3/50; G01J 3/511
[52] U.S. Cl. ..................................... 250/226; 356/416
[58] Field of Search ........................ 250/226, 339, 341; 356/407, 414, 416, 425, 319, 408, 434, 433

[56] References Cited

U.S. PATENT DOCUMENTS

| 3,436,556 | 4/1969 | McCartney | 250/226 |
| 3,751,643 | 8/1973 | Dell et al. | 356/319 |
| 4,132,314 | 1/1979 | von Beckman et al. | 356/407 |
| 4,170,987 | 10/1979 | Anselmo et al. | 356/416 |
| 4,300,689 | 11/1981 | Franklin et al. | 356/418 |
| 4,458,323 | 7/1984 | Willis et al. | 356/323 |
| 4,482,251 | 11/1984 | Saylor | 356/418 |

Primary Examiner—David C. Nelms
Assistant Examiner—Michael Messinger
Attorney, Agent, or Firm—Kenyon & Kenyon

[57] ABSTRACT

A method and apparatus for the photometric measurement of the transmission or reflection of radiation on a test specimen or measuring object, especially for the final automatic inspection or quality control, for instance, of vacuum-deposited discs with respect to uniformly of the coating or the like, comprises a photometer with a chopper disc in the ray path and with at least one detector (sensor) and a detector amplifier (measuring signal amplifier). In order to achieve that the measurement can be employed under production conditions in on-line operation on moving measuring objects reliably for a long time, the invention provides that the measuring signals are numerically determined directly at the output of each detector amplifier by a fast analog-to-digital conversion and are subsequently processed further in two stages exclusively digitally by peak value determination, combined with averaging, within at least two chopper periods to form a transmission or reflection measurement value. The absolute value of the light intensity at the detector measured in a preceding chopper period serves as reference for the formation of the quotient in the determination of the transmission or reflection.

13 Claims, 2 Drawing Sheets

METHOD AND APPARATUS FOR THE ON-LINE MEASUREMENT OF TRANSMISSION OR REFLECTION ON MOVING OBJECTS IN THE RANGE OF DETECTABLE ELECTROMAGNETIC RADIATION

BACKGROUND OF THE INVENTION

The invention relates to a transmission and/or reflection measuring method and apparatus, especially for the automatic final inspection or quality test of vacuum-deposited discs (plate glass) or similar substrates with respect to the uniformity of applied thin layers (coatings) and the maintenance of specified transmission and reflection tolerances for fixed wavelengths or different colors.

For obtaining specified optical properties, for instance, the refining of plate glass, suitable materials are applied on base bodies in thin films. The control of the transmission or reflection properties achieved is customarily carried out locally limited and off-line, usually by sampling. To this end, prepared samples or test specimens of the material to be characterized or tested are placed as a rule in the measuring volume of laboratory photometers. These photometers consist of optical arrangements with a light source which covers the required wavelength range; lenses for collimating and directing the measuring rays; a chopper, for instance, a chopper disc; optically a ray divider in the measuring ray; filters or optical grids for filtering out a predetermined measuring light wavelength behind the test specimen; detectors for generating a measuring signal proportional to the intensity of the measuring ray; and detector amplifiers for amplyifying the measuring signal of the detectors, and of a circuit for the subsequent analog signal evaluation. The use of such photometers for the on-line control of transmission or reflection on moving objects has not been possible to date.

Measurements at edge zones of the samples to be tested or test specimens are not possible. The local resolution in extensive measuring zones is only small. Because of the usually used a-c voltage amplifiers, the accuracy of the measurement is determined by the stability of the chopping frequency. This stability requirement can be met only with difficulty under industrial operating conditions.

Further limitations for conventional photometers in the production process are due to unavoidable soiling which affects the optical components, due to drift as a result of external influences such as temperature and variations, etc., as well as aging of lamps, detectors and other components.

It is an object of the invention to develop the photometric measurement of the transmission of or reflection at test specimens or measuring objects, especially coated glasses or substrates, in the range of detectable electromagnetic radiation, especially light, for determination or quality control of the samples to be tested, with respect to method and apparatus in such a manner that it becomes usable reliably over the long term under production conditions in on-line operation on moving objects.

SUMMARY OF THE INVENTION

A method for photometrically determining optical properties of a test specimen comprises, in accordance with the present invention, the steps of (a) transmitting through or reflecting from the test specimen a light beam having a range of detectable frequencies, (b) periodically interrupting the light beam prior to impingement thereof on the test specimen, (c) filtering the light beam, upon transmission thereof through or reflection thereof from the test specimen, to obtain essentially a single wavelength beam of light, and (d) focusing the single wavelength beam, the single wavelength beam having an intensity determined in part by optical characteristics of the test specimen. The method pursuant to the invention further comprises the steps of (e) sensing the intensity of the focused single wavelength beam, (f) generating an electrical analog signal proportional to the intensity, and (g) converting the analog signal to a digital signal. It should be specifically noted that each single frequency beam path has only one optical path and this one path is able to provide sufficient information to calculate all necessary reference signals for compensating for long-term drift effects.

During a period of continuous impingment of the light beam on the test specimen to obtain a plurality of sample intensity values, the digital signal is sampled at a sampling frequency selected so that first and last sample intensity values of a predetermined number of consecutive ones of the sample intensity values are separated in time from one another by at most half of the period of continuous light impingement. A first average intensity value is then automatically calculated from the consecutive ones of the sample intensity values.

In other steps, the digital signal is also sampled during a period of continuous interruption of the light beam substantially contiguous in time with the period of continuous impingement of the light beam to obtain a plurality of additional sample intensity values, the period of continuous interruption being at least as long as the period of continuous impingement. The additional sampling occurs at the sampling frequency, whereby first and last sample intensity values of the predetermined number of consecutive ones of the additional sample intensity values are separated in time from one another by less than half of the period of continuous interruption. A second average intensity value is automatically calculated from the consecutive ones of the additional sample intensity values. The processing of the light signal results in a digital filtering of the signal whereby the mean value of each measuring point and its neighbor replaces each measuring point, without the necessity of dividing the signal into reference, dark and sample signals.

In a subsequent step in a method according to the invention, a background corrected light intensity value associated with the test specimen is automatically calculated from the first average intensity value and the second average intensity value. A quotient of the background corrected light intensity value and a predetermined background corrected reference light intensity value associated with the light beam at the wavelength of the single wavelength beam is then automatically calculated. The calculation of the background-corrected light intensity by peak value formation of the mean values over a time period greater than half of the chopper period is performed without any time connections to dark, sample and/or reference signals.

An apparatus for photometrically determining optical properties of a test specimen comprises, in accordance with the present invention, a light source for producing a light beam having a range of detectable frequencies, a beam interrupter for periodically interrupting the light beam prior to impingement thereof on the test specimen, a light guide for directing the light beam to the test specimen, a filter for filtering the light beam, upon impingement thereon on the test specimen, to obtain essentially a single wavelength beam of light, and a lens for focusing for focusing the single wavelength beam, the single wavelength beam having an intensity determined in part by optical characteristics of the test specimen. A detector is provided for sensing the intensity of the focused single wavelength beam and for generating an electrical analog signal proportional to the intensity, while an analog-to-digital converter is operatively connected to the detector for converting the analog signal to a digital signal.

A sampling device is operatively connected to the analog-to-digital converter for sampling the digital signal at a sampling frequency during a period of continuous impingement of the light beam on the test specimen to obtain a plurality of first sample intensity values and for further sampling the digital signal at the sampling frequency during a period of continuous interruption of the light beam substantially contiguous in time with the period of continuous impingement of the light beam to obtain a plurality of second sample intensity values. The period of continuous interruption is at least as long as the period of continuous impingement and the sampling frequency is selected so that first and last sample intensity values of a predetermined number of consecutive ones of the first sample intensity values are separated in time from one another by at most half of the period of continuous impingement of the light beam on the test specimen and so that first and last sample intensity values of the predetermined number of consecutive ones of the second sample intensity values are separated in time from one another by less than half of the period of continuous interruption.

A computer is operatively connected to the sampling device for automatically calculating a first average intensity value from the consecutive ones of the first sample intensity values, for automatically calculating a second average intensity value from the consecutive ones of the second sample intensity values, for automatically calculating from the first average intensity value and the second average intensity value a background corrected light intensity value associated with the test specimen, and for automatically calculating a quotient of the background corrected light intensity value and a predetermined background corrected reference light intensity value associated with the light beam at the wavelength of the single wavelength beam.

The method and the photometer according to the invention are capable in on-line operation to execute the necessary measurements on the moving object fast, to detect reliably and independently of variations of the chopper frequency, to eliminate all possible interference parameters such as stray radiation (residual light), drift including aging and/or continuous soiling, to recognize independently the boundaries on the moving object in order to delineate the measuring process, as well as working out automatically measuring positions referred to the boundaries.

The generated measuring signals are numerically determined immediately at the output of each detector amplifier by fast analog-to-digital conversion and are subsequently combined, exclusively digitally, by determining peak values with averaging within at least two chopper periods and are processed further in two stages to form a measured transmission or reflection value. As a reference for forming the quotient (transmission and reflection are relative numbers) serves the absolute value of the light intensity at the detector as measured in a previous chopper period. The measuring signal is numerically averaged in a manner known per se so that the actual measurement values $J(t_i)$ are replaced by averaged measurement values $J^*(t_i)$ according to $$J^*(T_i) = \frac{1}{2k+1} \sum_{j=-k}^{k} J(t_{i+j}) \quad (1)$$

The number of the measurement points k included in the respective averaging is determined via the measuring frequency f from the minimum plateau width b in such a manner that the number k of the measurement values included in the averaging occupies less or at most one-half of the plateau width b. It is ensured thereby that in the case of trapezoidal detector signals (as a result of the customary design of the chopper disc), the level of the plateau is correctly simulated for at least one value and interference is attenuated at the same time with the attenuation factor D $$D = \frac{1}{2k+1} \quad (2)$$

For determining the desired peak value, this method is applied to at least one chopper period $1/f_c$, so that the maximum and the minimum can be determined unequivocally and independently of the starting point in time. The difference of the maximum and the minimum yields the desired intensity difference $\Delta J$.

The measuring frequency f (repetition rate of the measurements) will therefore reach the chopper frequency $f_c$ in the best case. Variations $\Delta f_c$ of the chopper frequency are without influence on the measuring result here, as long as the actual chopper frequency $(f_c + \Delta f_c)$ remains below that frequency in which $(2k+1)$ amounts to just half the plateau width.

The method for numerical determination of the transmission T works in two stages. In the first stage, the actual chopper frequency $f_c$ is determined in the free ray path (no measuring object present), the corresponding measuring time $T_{mess} > T_{chopp} + \Delta T_{chopp}$ and the width of the bright/dark plateau b is measured and therefrom, the average interval is derived as the number of measuring points k to be included in the averaging, and subsequently, the peak value determination for determining the unattenuated intensity $I_o = \Delta J_o$ as the normalizing quantity is completed with the formation of the mean value.

In the second stage, the measuring object is placed in the ray path so that after the peak values are determined by analog means, the intensity $I = \Delta J$ attenuated by the sample is determined and the desired transmission $T = I/I_o$ is digitally computed with the normalizing quantity $I_o$ known from the first stage.

In both stages, measurements are performed quasi continuously. The automatic switching from the first stage to the second stage can take place if the transmission $T_i$ (or reflection) calculated from two successive values $$T_i = \frac{I_i}{I_{i-1}}$$

fails below a preset threshold value $T_s$. The intensities $I_{i+n}$ (n>0) measured in the second stage are accordingly normalized for calculating the transmission $T_{i+n}$ to an intensity undisturbed with certainty $I_{i-m}$ (m>0) of the first stage.

The automatic switching back from the second stage to the first stage can be accomplished accordingly if the preset threshold value $T_s$ is exceeded.

The invention permits fast measurements also in border zones of the test sepcimens and achieves high resolution in extensive measuring zones, the chopper period having to meet no particular stability requirements. Before each measurement, a calibration can be performed and edges (or heights) of test specimens can be recognized, for instance, for automatically fixing measuring positions. Because of the high measuring rate, transport velocity of the test specimens up to 40 m/min are possible with distance of the test specimen of 5 cm. Double detectors with standard wavelengths of 550 nm (green), 660 nm (red), and 2,000 nm (infrared) can be used. Compensation of stray light is possible.

With the invention, the light permeability (transmission) for light of different colors (wavelengths) can be measured fast on-line at several places of a disc so that these values can be checked as to maintaining presettable tolerances. The measurement can be made with automatic boundary or edge recognition also continuously on particularly fast moving consecutive discs on line.

The electricity obtained measuring results can be displayed on a picture screen as numerical values within the schematized disc contours at the respective measuring points (bottom, center, top). The sizes of the discs and the corresponding measuring positions can be reproduced in such a manner that the correlation of the measured values to the measurement objects is provided to the user directly.

The measured values can be printed out on a readout print with comments on supplementing information regarding glass type, lot, date, time of day, etc.

BRIEF DESCRIPTION OF THE DRAWING

An embodiment example of the invention will be explained in greater detail by further embodiments, making reference to a drawing, in which.

DETAILED DESCRIPTION

Figure 1:
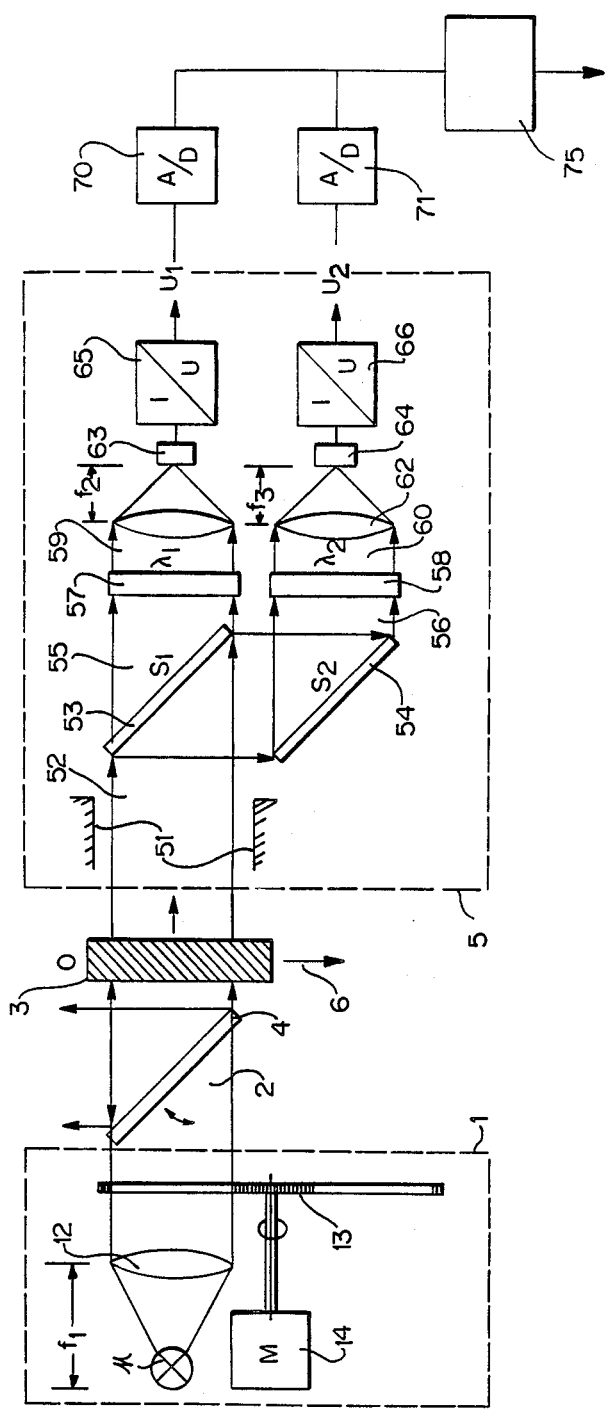
FIG. 1 shows a schematic view of a measuring device according to the invention, and FIG. 2, a time/intensity diagram of the measurement signal present at the detector unit.

The measuring device comprises a light source 1 and a detector unit 5 for measuring a test specimen or measuring object 3 placed between them or into the measuring light ray 2. If a test specimen 3, for instance, a glass pane moves into the measuring light ray 2 in the direction of the arrow 6 between the light source 1 and the detector unit 5, the intensity of the light is attenuated from the starting value $I_o$ to the value I. The measurement is made of the transmission of the glass pane defined via $T=I/I_o$ for different wavelengths $\lambda$. As a light source serves the 6-volt, 6-watt incandescent lamp 11. In certain cases it can be replaced by a laser light source. It is supplied with a d-c voltage of 5 V±0.01 V. Due to the operation at reduced voltage, the life of the incandescent lamp is increased, for one, and secondly, the maximum of the spectral distribution of the incandescent lamp 11 can be shifted further toward infrared. The light of the incandescent lamp 11 is directed by a bi-convex condeser lens 12 with a focal length $f_1=40$ mm parallel to the entrance aperture of a dector unit 5. It is periodically interrupted by a two-vane rotating chopper disc 13. This chopper disc 13 is put in rotation by a d-c motor 14 and rotates at approximately 25 $s^{-1}$. The speed is stabilized, using an integrated motor control circuit, for instance, TDA1559. The measuring light ray 2 leaving the light source 1 is therefore chopped periodically at approximately 50 Hz.

In the arrangement shown, the chopped measuring light beam 2 penetrates the test speciment 3 and arrives at the detector unit 5 for measuring the transmission. For measuring reflection, the measuring light ray 2 first passes, ahead of the test specimen, an additional mirror 4 which can be swung out of the ray path; is then reflected at the test specimen 3 and then gets through reflection at the mirror 4 to another detector unit, not shown, which is identical with the detector unit 5.

For reducing stray light influences on the penetrating light-measuring ray 52 on the measuring signal, a light protection tube 51 is provided on the input side. The direct light measuring ray 52, after passing through the light protection tube 51, gets to another ray divider 53 which is arranged at 45° to the direction of the rays. The deflected part of the direct light measuring ray 56 strikes a further mirror 54, which is likewise arranged at 45° relative to the direction of the rays. The beam divider 53 is here a beam divider plate with an intensity division ratio of 50:50 between transmission and reflection. The mirror 54 is a totally reflecting first-surface plane mirror. The measuring light rays 55 and 56 leaving the beam divider 53 and the mirror 54 arrive at interference filters 57 and 58, respectively, which pass only filtered transmission light rays 59 and 60 of the desired wavelength $\lambda_1$ and $\lambda_2$. These monochromatic direct-light measuring rays 59 and 60 are focused by means of further biconvex condenser lenses 61 and 62 on the active surfaces of sensors or detectors 63 and 64. The condenser lenses 61 and 62 have the focal lengths $f_2$ and $f_3$ for the wavelengths $\lambda_1$ and $\lambda_2$. The detectors 63 and 64 are immediately followed by current/voltage converters as detectors amplifiers 65 and 66 which furnish currents proportional to the intensities incident on the detectors 63 and 64 into normalized voltages $U_1$ and $U_2$ (0 ... +10 V). They consist of two-stage d-c coupled amplifier stages on the basis of an operational amplifier, for instance, AD 547 J H. By dividing the direct light measuring ray 52 emerging from the test specimen 3 into two monochromatic direct light measuring rays 59 and 60, two measurements with different wavelengths can be carried out from the same measuring location. This measuring beam 52 can also be divided into n further mesuring rays, each of which falls on a detector through a filter of different wavelength, so that also a spatial test of the coating of the test specimen at the measuring location can be carried out because the observation and imagining points of the individual light frequencies have different distances from the imaging lenses 61, 62.

Silicon photo diodes are used as dectors 63 and 64 for the wavelengths $\lambda_1$, $\lambda_2$ in the range of visible light (for instance, Type OSD 15-5 T). For $\lambda_1$ in the near infrared ($\lambda_1=2,000$ nm), an InAs detector (indiumarsenide photodiode) is used (for instance, Type J 12-5, 2 mm). In addition, an Si(111) disc, 3 mm thick and polished on both sides is used as the beam divider plate 53 which exhibits high transmission for $\lambda_1=2,000$ nm, but high reflection for visible light. This arrangement permits a very fast measurement in the infrared light range simultaneously with the measurement in the visible light range.

Each detector amplifier 65 and 66 is directly followed by an analog-to-digital converter 70 and 71, respectively, which converts the analog measuring signal present at its output into a digitalized measuring signal. To the A/D converters 70 and 71, a process computer 75 is connected which determines the wanted transmission or reflection according to the method of the invention from the digitalized measurement values.

Figure 2:
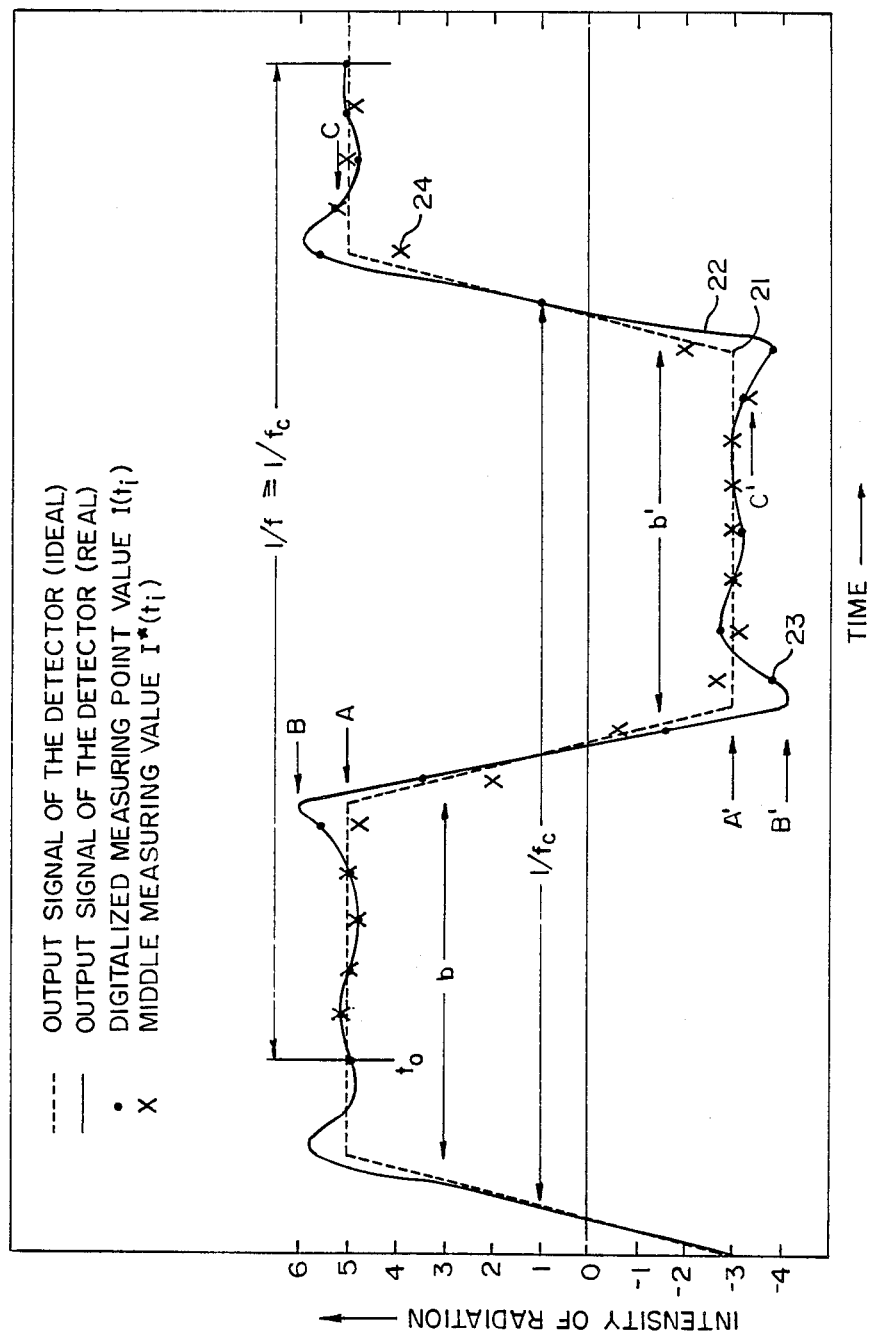

The waveform of the measurement or output voltage $U_1$ of the detector amplifier 65 which is trapezoidal because of the chopper disc 13 and the amplifier of which corresponds to the intensity corrected by the residual light share, is shown schematically in FIG. 2. Since the residual light is added to the measuring signal in the same manner during the dark phase as well as the bright phase of the chopper disc 13, the amplitude (i.e., the difference between the upper and the lower plateau) is not changed. The minimum measuring time is therefore given substantially by the chopper frequency and is only 20 ms at 50 Hz.

The dashed line 21 in FIG. 2 shows the idealized waveform as is seen within a chopper period $1/f_c$ if the apertures of the chopper disc are large as compared to the aperture of the biconvex condenser lense 12. The solid line 22 represents a possible real measuring signal which was drawn with heavy distortions from the idealized shape of the line 21, for illustrating the method. The intensity $I(\lambda_1)$ stemming from the incandescent lamp 11 is calculated from the difference of the intensities between the bright and the dark rays, i.e., idealized from A-A'. In order to approach the values A and A' as closely as possible for a real signal, the measuring signal is digitalized with a constant scanning frequency $f_a$ starting at the time $t_0$ (points 23). Then, these measurement values $I(t_i)$ are replaced by mean values $J^*(t_i)$ within the measurement period $1/f$ which is larger than- /or at best equal to the chopper period $1/f_c$ (crosses 24, shown for averaging over 3 adjacent points, i.e., k=1). The average formation is carried out according to equation (1)

$$J^*(T_i) = [1/(2k + 1)] \sum_{j=-k}^{j=k} J(t_{i+j})$$

i.e., k measuring points to the left and right of the measuring point to be processed are included in the averaging. k is determined here in a preceding phase from the measuring signal in such a manner that 2k +1 measuring points are with certainty less than one-half of the plateau widths b and b'. It is assured thereby that, independently of $t_0$, for $f<f_c$, basically at least once, 2k+1 measuring points come to lie on the upper (bright) and the lower (dark) plateau.

The intensity I ($80_1$) stemming from the incandescent lamp 11 is accordingly calculated approximately by determining the peak value from max $(I^*)$−max $(I^*)$− min $(I^*)$=C−C'. By the averaging method described, interference influences are suppressed at least with the attenuation factor D=1/(2k+1) (equation 2). The difference of the real peak values B−B', on the other hand, deviates substantially more from the ideal value A−A'. Variations of the chopper frequency $f_c$ remains without effect as long as f is smaller than $f_c$ and 2k+1 measuring points come to lie on at least one-half of the plateau.

The method for the numerical determination of the transmission T (or reflection) operates in two stages. In the first stage, the measuring device is calibrated in the chopped free ray path (no measuring object). In this process, the measuring period 1/f, the averaging interval 2k+1 as well as the intensity $I_0$ corresponding to 100% transmission are determined. To this end, the output signal of the detector amplifiers 65, 66 is digitalized with the scanning frequency $f_a$ over a time period which is with certainty longer than the chopper period. Then, the maximum $J_{max}$ and the minimum $J_{min}$ are determined from these measurement values. From this, the mean value $J_M=(J_{max}+J_{min})/2$ is formed. The signal thus varies periodically about this mean value. A chopper frequency $f_c$ is determined from a number n of measuring points digitalized with a constant scanning frequency $f_a$ in such a manner that the counting of the points begins at the instant when the mean value $J_M$ is exceed for the first time, and the counting is terminated when, after the signal falls below the mean value, it exceeds it again. We have $f_c<f_a/n$. Similarly, the plateau widths b and b' and therefrom, k can be determined. The measuring frequency f is chosen so that f is in principle smaller than $f_c$, also for expected variations of $f_c$. The procedure for calculating k is similar. Thus, all variables for the numerical determination of the $I_0$ value by means of the peak value determination described above in connection with the averaging are fixed, and $I_0$ can be determined.

In the second stage, the measuring object 3 is inserted into the ray path, so that after the determination of the peak value with averaging, the attenuated intensity I with f can now be determined. Together with the previously determined normalizing quantity $I_0$, the wanted transmission $T=I/I_0$ can be calculated digitally therefrom.

In both stages the measurements are made quasi continuously. Automatic switching from the first stage to the second stage takes place if a measuring object 3 is inserted into the measuring light ray 2. The resetting takes place when the measuring object leaves the measuring light ray. Without a measuring object in the measuring light ray, the measuring device therefore calibrates itself anew continuously. With the measuring object in the measuring light ray, transmissions are determined and stored continuously. With constant velocity of the measuring object, the transmission is therefore measured at equidistant measuring positions thereon, for instance, of a disc.

The detection as to whether a measuring object is in the ray path, takes place either by a capacitive proximity switch which is arranged so that it reports the measuring object 3 exactly at the instant at which the latter is in the optical ray path, or by the measuring arrangement itself.

In the latter case, quotients $T_i=I_i/I_{i-1}$ are continuously determined from successive intensities $I_i$, $I_{i-1}$. If $T_i$ falls below a given threshold value $T_s$, then a measuring object is in the ray path. The transmissions $T_{i+m}$(m 0) are calculated with a reference value $I_0$ which was measured so far below $I_i$ that it was not yet influenced by the edges of the measuring object with certainty.

The resetting takes place correspondingly if the transmission exceeds the presettable threshold value $T_s$. While the measuring object is in the ray path, all transmission values can be stored continuously. When the measuring object has left the ray path, an unequivocal local correlation of the transmission values and the positions on the measuring object can be made from the velocity v of the measuring object and the number of transmission values as well as the scanning frequency $f_a$. In particular, transmissions in predeterminable areas (for instance, the edge regions) can be selected or local mean values can be calculated and check for maintenance of specified tolerances.

For applications, in which the velocity v varies, for instance, depending on the lot, it can be provided that v is determined automatically from the time difference between the response of two capacitive proximity switches arranged at the distance d.

In FIG. 2 a is the output signal of the detector preamplifier (ideal), b is the output signal of the detector preamplifier (real), c are digitalized measuring points I ($t_i$), d are averaged measurement values: I* ($t_i$), e bright, f dark, g time and h intensity of the radiation.

I claim:

1. A method for photometrically determining optical properties of a test specimen, comprising the steps of:
    transmitting through or reflecting from said test specimen a light beam having a range of detectable frequencies;
    periodically interrupting said light beam prior to impingement thereof on said test specimen;
    filtering said light beam, upon transmission thereof through or reflection thereof from said test specimen, to obtain essentially a single wavelength beam of light;
    focusing said single wavelength beam, said single wavelength beam having an intensity determined in part by optical characteristics of said test specimen;
    sensing said intensity of the focused single wavelength beam;
    generating an electrical analog signal proportional to said intensity;
    converting said analog signal to a digital signal;
    sampling said digital signal during a period of continuous impingement of said light beam on said test specimen to obtain a plurality of sample intensity values, said step of sampling occurring at a sampling frequency selected so that first and last sample intensity values of a predetermined number of consecutive ones of said sample intensity values are separated in time from one another by at most half of said period;
    automatically calculating a first average intensity value from said consecutive ones of said sample intensity values;
    further sampling said digital signal during a period of continuous interruption of said light beam substantially contiguous in time with said period of continuous impingement of said light beam to obtain a plurality of additional sample intensity values, said period of continuous interruption being at least as long as said period of continuous impingement, said step of further sampling occurring at said sampling frequency, whereby first and last sample intensity values of said predetermined number of consecutive ones of said additional sample intensity values are separated in time from one another by less than half of said period of continuous interruption;
    automatically calculating a second average intensity value from said consecutive ones of said additional sample intensity values;
    automatically calculating from said first average intensity value and said second average intensity value a background corrected light intensity value associated with said test specimen;
    automatically calculating a quotient of said background corrected light intensity value and a predetermined background corrected reference light intensity value associated with said light beam at the wavelength of said single wavelength beam; and
    wherein said focusing, sensing, generating, converting, sampling, calculating, further sampling and further calculating steps are preformed upon signals obtained from the same light path.

2. The method set forth in claim 1, further comprising the steps of inserting said test specimen into a path of said light beam and determining said reference light intensity value prior to the insertion of said test specimen into said path.

3. The method set forth in claim 2 wherein said step of periodically interrupting is performed by rotating a chopper disc through said light beam, said period of continuous impingement constituting a period during which said light beam is transmitted past said disc, said period of continuous interruption constituting a period during which said light beam is blocked by said disc.

4. The method set forth in claim 3 wherein said steps of sampling and further sampling are performed during one cycle of rotation of said disc and said step of determining said reference light intensity value is performed during another cycle of rotation of said disc.

5. The method set forth in claim 4 wherein said other cycle is prior to said one cycle.

6. The method set forth in claim 1, further comprising the steps of subdividing said light beam prior to said step of filtering to produce another light beam and filtering said other light beam to obtain another single wavelength beam of light, said steps of focusing, sensing, generating and converting being performed on said other single wavelength beam of light.

7. An apparatus for photometrically determining optical properties of a test specimen, comprising in combination;
    light source means for producing a light beam having a range of detectable frequencies;
    means for periodically interrupting said light beam prior to impingement thereof on said test specimen;
    means for directing said light beam to said test specimen;
    filter means for filtering said light beam, upon impingement thereof on said test specimen, to obtain essentially a single wavelength beam of light;
    focusing means for focusing said single wavelength beam, said single wavelength beam having an intensity determined in part by optical characteristics of said test specimen;
    detector means for sensing said intensity of the focused single wavelength beam and for generating an electrical analog signal proportional to said intensity;
    analog-to-digital conversion means operatively connected to said detector means for converting said analog signal to a digital signal;
    sampling means operatively connected to said analog-to-digital conversion means for sampling said digital signal at a sampling frequency during a period of continuous impingement of said light beam on said test specimen to obtain a plurality of sample intensity values and for further sampling said digital signal at said sampling frequency during a period of continuous interruption of said light beam substantially contiguous in time with said period of continuous impingement of said light beam to obtain a plurality of additional sample intensity values, said period of continuous interruption being at least as long as said period of continuous impingement, said sampling frequency being selected so that first and last sample intensity values of a predetermined number of consecutive ones of said sample intensity values are separated in time from one another by at most half of said period and so that first and last sample intensity values of said predetermined number of consecutive ones of said additional sample intensity values are separated in time from one another by less than half of said period of continuous interruption; and computation means operatively connected to said sampling means for automatically calculating a first average intensity value from said consecutive ones of said sample intensity values, for automatically calculating a second average intensity value from said consecutive ones of said additional sample intensity values, for automatically calculating from said first average intensity value and said second average intensity value a background corrected light intensity value associated with said test specimen, and for automatically calculating a quotient of said background corrected light intensity value and a predetermined background corrected reference light intensity value associated with said light beam at the wavelength of said single wavelength beam.

8. The apparatus set forth in claim 7, wherein said means for periodically interrupting includes a rotatable of chopper disc disposed in a path of said light beam, said period of continuous impingement constituting a period during which said light beam is transmitted past said disc, said period of continuous interruption constituting a period during which said light beam is blocked by said disc.

9. The apparatus set forth in claim 8, further comprising:
means for subdividing said light beam, upon impingement thereof on said test specimen and prior to said step of filtering, to produce another light beam;
additional filter means for filtering said other light beam, upon impingement thereof on said test specimen, to obtain another single wavelength beam of light;
additional focusing means for focusing said other single wavelength beam, said other single wavelength beam having an associated intensity determined in part by optical characteristics of said test specimen;
additional detector means for sensing said associated intensity of the focused other single wavelength beam and for generating another electrical analog signal proportional to said associated intensity; and
additional analog-to-digital conversion means operatively connected to said additional detector means for converting said other analog signal to an associated digital signal, said additional analog-to-digital conversion means being operatively connected to said sampling means for transmitting said associated digital signal thereto.

10. The apparatus set forth in claim 9 wherein said detector means includes an indium-arsenide photodiode for measurement in an infrared electromagnetic energy frequency range.

11. The apparatus set forth in claim 10 wherein said means for subdividing includes a silicon disc.

12. The apparatus set forth in claim 11 wherein said silicon disc is a silicon (111) disc.

13. The apparatus set forth in claim 7 wherein said detector means includes an indium-arsenide photodiode for measurement in an infrared electromagnetic energy frequency range.

* * * * *

UNITED STATES PATENT AND TRADEMARK OFFICE
CERTIFICATE OF CORRECTION

PATENT NO. : 4,785,170

DATED : November 15, 1988

INVENTOR(S) : Wolfgang F. Witt

It is certified that error appears in the above-identified patent and that said Letters Patent is hereby corrected as shown below:

Abstract:
Lines 9-10, change "In order to achieve that the measurement can be employed" to -- To allow the measurement --.

Col. 1, line 29, change "optically" to -- optionally --.
    line 30, change "ray;" to -- ray path behind the test specimen position, for dividing the measuring ray; --
    line 55, change "at" to -- of --.

Col. 3, line 4, change "thereon" to -- thereof --.
    line 6, delete "for focusing" (2X).
    line 52, change "are capable" to -- can --;
        delete "to".
    line 60, change "referred" to -- referring --.

Col. 4, line 20, change "plataeu" to -- plateau --.
    line 67, change "fails" to -- falls --.

Col. 5, line 8, change "sepcimens" to -- specimens --.
    line 25, delete "also".
    line 28, change "electricity" to -- electrically --.
    line 37, change "on supplementing" to -- and supplementary --.
    line 68, change "condeser" to -- condenser --.

Col. 6, line 1, change "dector" to -- detector --.
    line 29, change "first" to -- flat --.
    line 41, change "detectors" to -- detector --.
    line 52, change "mesuring" to -- measuring --.
    line 56, change "imagining" to -- imaging --.
    line 59, change "dectors" to -- detectors --.

UNITED STATES PATENT AND TRADEMARK OFFICE
CERTIFICATE OF CORRECTION

PATENT NO. : 4,785,170

DATED : November 15, 1988

INVENTOR(S) : Wolfgang F. Witt

It is certified that error appears in the above-identified patent and that said Letters Patent is hereby corrected as shown below:

Col. 7, line 26, change "lense" to -- lens --.
lines 38-39, change "than-/or" to -- than or --.

line 57, change "$80_1$" to -- $\lambda_1$ --.
line 59, delete "max (I*)— -".

Col. 7, line 65, change "remains" to -- remain --.

Col. 8, line 19, change "exceed" to -- exceeded --.

Col. 9, line 6, change "check" to -- checked --.
line 13, change "2a" to -- 2, a --.

Col. 11, line 37, delete "of".

Signed and Sealed this

Fifth Day of September, 1989

*Attest:*

DONALD J. QUIGG

*Attesting Officer*  Commissioner of Patents and Trademarks